(12) United States Patent
Humphreys

(10) Patent No.: US 9,045,529 B2
(45) Date of Patent: Jun. 2, 2015

(54) DISULFIDE STABILIZED ANTIBODIES AND FRAGMENTS THEREOF

(75) Inventor: David Paul Humphreys, Slough (GB)

(73) Assignee: UCB PHARMA S.A., Brussels (BE)

( * ) Notice: Subject to any disclaimer, the term of this patent is extended or adjusted under 35 U.S.C. 154(b) by 86 days.

(21) Appl. No.: 13/637,209

(22) PCT Filed: Mar. 25, 2011

(86) PCT No.: PCT/GB2011/050608
§ 371 (c)(1),
(2), (4) Date: Dec. 17, 2012

(87) PCT Pub. No.: WO2011/117648
PCT Pub. Date: Sep. 29, 2011

(65) Prior Publication Data
US 2013/0108622 A1    May 2, 2013

(30) Foreign Application Priority Data

Mar. 25, 2010   (GB) ................................ 1005064.9

(51) Int. Cl.
*A61K 38/00*   (2006.01)
*C07K 16/00*   (2006.01)

(52) U.S. Cl.
CPC .............. *C07K 16/00* (2013.01); *C07K 2317/55* (2013.01); *C07K 2317/94* (2013.01)

(58) Field of Classification Search
CPC ............ A61K 2039/505; A61K 38/00; A61K 2300/00; A61K 39/395; C07K 2317/24; C07K 2317/56; C07K 2317/55
See application file for complete search history.

(56) References Cited

U.S. PATENT DOCUMENTS

| | | |
|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbus et al. |
| 5,661,016 A | 8/1997 | Lonberg et al. |
| 5,667,425 A | 9/1997 | Pineau et al. |
| 5,677,425 A | 10/1997 | Bodmer et al. |
| 5,698,426 A | 12/1997 | Huse |
| 5,733,743 A | 3/1998 | Johnson et al. |
| 5,747,654 A * | 5/1998 | Pastan et al. ............... 530/391.7 |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,331,415 B1 | 12/2001 | Cabilly et al. |
| 6,642,356 B1 | 11/2003 | Humphreys |
| 8,053,562 B2 * | 11/2011 | Humphreys ............... 530/387.3 |
| 2007/0092940 A1 * | 4/2007 | Eigenbrot et al. ........... 435/69.1 |

FOREIGN PATENT DOCUMENTS

| | | |
|---|---|---|
| EP | 0392745 | 10/1990 |
| EP | 0438474 | 7/1991 |
| EP | 0463151 | 1/1992 |
| EP | 0546073 B1 | 6/1993 |
| WO | WO8601533 | 3/1986 |
| WO | WO9002809 | 3/1990 |
| WO | WO9109967 | 7/1991 |
| WO | WO9110737 | 7/1991 |
| WO | WO9201047 | 1/1992 |
| WO | WO9202551 | 2/1992 |
| WO | WO9218619 | 10/1992 |
| WO | WO9222583 | 12/1992 |
| WO | WO9306231 | 4/1993 |
| WO | WO9311236 | 6/1993 |
| WO | WO9515982 | 6/1995 |
| WO | WO9520401 | 8/1995 |
| WO | WO9820734 | 5/1998 |
| WO | WO9825971 | 6/1998 |
| WO | WO8900195 | 1/1999 |
| WO | WO8901476 | 2/1999 |
| WO | WO9915549 | 4/1999 |

(Continued)

OTHER PUBLICATIONS

Rothlisberger et al (Journal of Molecular Biology, 2005, 347:773-789).*
Weisser et al (Biotechnology Advances, 2009, 27:502-520).*
Kohler, et al. Nature, 256:495-497 (1975).
Kozbor, et al., Immunology Today, 4:72 (1983).
Cole, et al., Monoclonal Antibodies and Cancer Therapy, pp. 77-96 (1985).
Babcook, J., et al. Proc. Natl. Acad. Sci., 93:7843-7848 (1996).
Brinkman, et al., J. Immunol. Methods, 182:41-50 (1995).
Ames, et al., J. Immunol. Methods, 184:177-186 (1995).
Kettleborough, et al., Eur. J.Immunol., 24:952-958 (1994).
Persic, et al., Gene, 187:9-18 (1997).
Burton, et al., Advances in Immunology, 57:191-280 (1994).
Ward, et al., Nature, 341:544 (1989).
Orlandi, et al., Proc. Natl. Acad. Sci., 86:3833 (1989).
Riechmann, et al., Nature, 322:323 (1988).
Bird, et al., Science, 242:423 (1988).
Mountain, et al., Biotechnol. Genet. Eng. Rev., 10:1-142 (1992).
Verma, et al., Journal of Immunological Methods, 216:165-181 (1998).
Schoonjans, et al., Journal of Immunology, 165: 7050-7057 (2000).
Zhu, et al., Protein Science, 6:781-788 (1997).

(Continued)

*Primary Examiner* — Sean Aeder
*Assistant Examiner* — Julie Wu
(74) *Attorney, Agent, or Firm* — McDonnell Boehnen Hulbert & Berghoff LLP

(57) ABSTRACT

The present disclosure provides an antibody or antibody fragment comprising at least one Fab molecule, wherein the light chain variable region, $V_L$ and the heavy chain region, $V_H$ of the Fab molecule are linked by one or more disulfide bonds, and use of the same in treatment or prophylaxis.

13 Claims, 2 Drawing Sheets

(56) References Cited

FOREIGN PATENT DOCUMENTS

| WO | WO03031581 | | 4/2003 |
|---|---|---|---|
| WO | WO2004051268 | | 6/2004 |
| WO | WO2005000899 | A2 | 1/2005 |
| WO | WO2005003169 | | 1/2005 |
| WO | WO2005003170 | | 1/2005 |
| WO | WO2005003171 | | 1/2005 |
| WO | WO2005117984 | | 12/2005 |
| WO | WO 2007010231 | A1 * | 1/2007 |
| WO | WO2007106120 | | 9/2007 |
| WO | WO2007109254 | A2 | 9/2007 |
| WO | WO2004106377 | | 12/2007 |
| WO | WO2008038024 | | 4/2008 |
| WO | WO2009040562 | A1 | 4/2009 |
| WO | WO2011030107 | A1 | 3/2011 |
| WO | WO2011036460 | A1 | 3/2011 |

OTHER PUBLICATIONS

Reiter, et al., Biochemistry, 33:5151-5459 (1994).
Reiter, et al., Journal of Biological Chemistry, 269:18327-18331 (1994).
Rajagopal, et al., Protein Engineering, 10:1453-1459 (1997).
Luo, et al., J. Biochem., 118:825-831 (1995).
Young, et al., FEBS Letters, 377:135-139 (1995).
Glockshuber, et al., Biochemistry, 29:1362-1367 (1990).
Brinkmann, et al., Proc. Natl. Acad. Sci., 90:7538-7542 (1993).
Jung, et al., Proteins, 19:35-47 (1994).
Wells, et al., Gene, 34:315-323 (1985).
Angal, et al., Molecular Immunology, 30:105-108 (1993).
Harris, R.J., Journal of Chromatography, 705:129-134 (1995).
Hellstrom, et al., Controlled Drug Delivery, pp. 623-653 (1987).
Thorpe, et al., Immunol. Rev., 62:119-58 (1982).
Dubowchik, et al., Pharmacology and Therapeutics, 83:67-123 (1999).
Chapman, Advanced Drug Delivery Reviews, 54:531-545 (2002).
Buchner, et al., Nature, 9:157-162 (1991).
Skerra, et al., Gene, 141:79-84 (1994).
Demarst, et al., Oxford University Press, 19:325-336 (2006).
Rothilsberger, et al., Journal of Molecular Biology, 347: 773-789 (2005).
Honegger, Handbook of Experimental Pharmacology,181:47-68 (2008).
Smith, et al., Bioconjugate Chemistry, 12:750-756 (2001).
Hust, et al., BMC Biotechnology, 7: p. 14 (2007).
Worn, et al., Journal of Molecular Biology, 305:989-1010 (2001).
Reiter, et al., Nature Biotechnology, 14:1239-1245 (1996).
Reiter, et al., Protein Engineering, 7:697-704 (1994).

* cited by examiner

Figure 1

497Fab-His

Heavy chain (SEQ ID NO:24)
EVQLVESGGGLVKPGGSLRLSCAASGVIFSDYYMAWVRQAPGKGLEWVGSI
NFAGDISYYRESVKGRFTISRDDSKNTLYLQMNSLKTEDTAVYYCTTDANRQ
NYDWFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNH
KPSNTKVDKKVEPKSCDKTHHHHHHHH Light chain (SEQ ID NO:25)
AIQLTQSPSSLSASVGDRVTITCKASESVSSSMYSYMHWYQQKPGKAPKLLIY
RASNLESGVPSRFSGSGSGTDFTLTISSLQPEDFATYYCQQSWTAPRTFGQGTK
VEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSF
NRGEC

497dsFab-His

Heavy chain (SEQ ID NO:26)
EVQLVESGGGLVKPGGSLRLSCAASGVIFSDYYMAWVRQAPGK<u>C</u>LEWVGSI
NFAGDISYYRESVKGRFTISRDDSKNTLYLQMNSLKTEDTAVYYCTTDANRQ
NYDWFAYWGQGTLVTVSSASTKGPSVFPLAPSSKSTSGGTAALGCLVKDYFP
EPVTVSWNSGALTSGVHTFPAVLQSSGLYSLSSVVTVPSSSLGTQTYICNVNH
KPSNTKVDKKVEPKSCDKTHHHHHHHH Light chain (SEQ ID NO:27)
AIQLTQSPSSLSASVGDRVTITCKASESVSSSMYSYMHWYQQKPGKAPKLLIY
RASNLESGVPSRFSGSGSGTDFTLTISSLQPEDFATYYCQQSWTAPRTFG<u>C</u>GTK
VEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSF
NRGEC

Figure 1 [cont'd]

652Fab-His

Heavy chain (SEQ ID NO:28)
QVTLKESGPVLVKPTETLTLTCTVSGFSLTNYHVQWIRQPPGKALEWLGVM
WSDGDTSFNSVLKSRLTISRDTSKSQVVLTMTNMDPVDTATYYCARDGTIAA
MDYFDYWGQGTLVTVSSASTKGPSVFPLAPSSKSTSGGTAALGCLVKDYFPE
PVTVSWNSGALTSGVHTFPAVLQSSGLYSLSSVVTVPSSSLGTQTYICNVNHK
PSNTKVDKKVEPKSCDKTHHHHHHHH Light chain (SEQ ID NO:29)
DIQMTQSPSSLSASVGDRVTITCLASEDISNYLAWYQQKPGKAPKLLIYHTSRL
QDGVPSRFSGSGSGTDFTLTISSLQPEDFATYYCQQGYRFPLTFGGGTKVEIKR
TVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGE
C

652dsFab-His

Heavy chain (SEQ ID NO:30)
QVTLKESGPVLVKPTETLTLTCTVSGFSLTNYHVQWIRQPPGKCLEWLGVMW
SDGDTSFNSVLKSRLTISRDTSKSQVVLTMTNMDPVDTATYYCARDGTIAAM
DYFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKP
SNTKVDKKVEPKSCDKTHHHHHHHH Light chain (SEQ ID NO:31)
DIQMTQSPSSLSASVGDRVTITCLASEDISNYLAWYQQKPGKAPKLLIYHTSRL
QDGVPSRFSGSGSGTDFTLTISSLQPEDFATYYCQQGYRFPLTFGQGTKVEIKR
TVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGE
C

SEQUENCE LISTING

```
<160> NUMBER OF SEQ ID NOS: 31

<210> SEQ ID NO 1
<211> LENGTH: 8
<212> TYPE: PRT
<213> ORGANISM: Artificial Sequence
<220> FEATURE:
<223> OTHER INFORMATION: Hinge Sequence

<400> SEQUENCE: 1

Asp Lys Thr His Thr Cys Ala Ala
1               5

<210> SEQ ID NO 2
<211> LENGTH: 11
<212> TYPE: PRT
<213> ORGANISM: Artificial Sequence
<220> FEATURE:
<223> OTHER INFORMATION: Hinge Sequence

<400> SEQUENCE: 2
```

```
Asp Lys Thr His Thr Cys Pro Pro Cys Pro Ala
1               5                   10
```

<210> SEQ ID NO 3
<211> LENGTH: 18
<212> TYPE: PRT
<213> ORGANISM: Artificial Sequence
<220> FEATURE:
<223> OTHER INFORMATION: Hinge Sequence

<400> SEQUENCE: 3

```
Asp Lys Thr His Thr Cys Pro Pro Cys Pro Ala Thr Cys Pro Pro Cys
1               5                   10                  15

Pro Ala
```

<210> SEQ ID NO 4
<211> LENGTH: 25
<212> TYPE: PRT
<213> ORGANISM: Artificial Sequence
<220> FEATURE:
<223> OTHER INFORMATION: Hinge Sequence

<400> SEQUENCE: 4

```
Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25
```

<210> SEQ ID NO 5
<211> LENGTH: 30
<212> TYPE: PRT
<213> ORGANISM: Artificial Sequence
<220> FEATURE:
<223> OTHER INFORMATION: Hinge Sequence

<400> SEQUENCE: 5

```
Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30
```

<210> SEQ ID NO 6
<211> LENGTH: 31
<212> TYPE: PRT
<213> ORGANISM: Artificial Sequence
<220> FEATURE:
<223> OTHER INFORMATION: Hinge Sequence

<400> SEQUENCE: 6

```
Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30
```

<210> SEQ ID NO 7
<211> LENGTH: 15
<212> TYPE: PRT
<213> ORGANISM: Artificial Sequence
<220> FEATURE:
<223> OTHER INFORMATION: Hinge Sequence

<400> SEQUENCE: 7

```
Asp Lys Thr His Thr Cys Cys Val Glu Cys Pro Pro Cys Pro Ala
1               5                   10                  15
```

<210> SEQ ID NO 8
<211> LENGTH: 26
<212> TYPE: PRT
<213> ORGANISM: Artificial Sequence
<220> FEATURE:
<223> OTHER INFORMATION: Hinge Sequence

<400> SEQUENCE: 8

```
Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25
```

<210> SEQ ID NO 9
<211> LENGTH: 11
<212> TYPE: PRT
<213> ORGANISM: Artificial Sequence
<220> FEATURE:
<223> OTHER INFORMATION: Hinge Sequence

<400> SEQUENCE: 9

```
Asp Lys Thr His Thr Cys Pro Ser Cys Pro Ala
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: Albumin Binding Peptide

<400> SEQUENCE: 10

```
Asp Leu Cys Leu Arg Asp Trp Gly Cys Leu Trp
1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: Albumin Binding Peptide

<400> SEQUENCE: 11

```
Asp Ile Cys Leu Pro Arg Trp Gly Cys Leu Trp
1               5                   10
```

<210> SEQ ID NO 12
<211> LENGTH: 15
<212> TYPE: PRT
<213> ORGANISM: Artificial Sequence
<220> FEATURE:
<223> OTHER INFORMATION: Albumin Binding Peptide

<400> SEQUENCE: 12

```
Met Glu Asp Ile Cys Leu Pro Arg Trp Gly Cys Leu Trp Gly Asp
1               5                   10                  15
```

<210> SEQ ID NO 13
<211> LENGTH: 20
<212> TYPE: PRT
<213> ORGANISM: Artificial Sequence
<220> FEATURE:
<223> OTHER INFORMATION: Albumin Binding Peptide

<400> SEQUENCE: 13

```
Gln Arg Leu Met Glu Asp Ile Cys Leu Pro Arg Trp Gly Cys Leu Trp
```

```
1               5                   10                  15
Glu Asp Asp Glu
            20
```

<210> SEQ ID NO 14
<211> LENGTH: 20
<212> TYPE: PRT
<213> ORGANISM: Artificial Sequence
<220> FEATURE:
<223> OTHER INFORMATION: Albumin Binding Peptide

<400> SEQUENCE: 14

```
Gln Gly Leu Ile Gly Asp Ile Cys Leu Pro Arg Trp Gly Cys Leu Trp
1               5                   10                  15
Gly Arg Ser Val
            20
```

<210> SEQ ID NO 15
<211> LENGTH: 21
<212> TYPE: PRT
<213> ORGANISM: Artificial Sequence
<220> FEATURE:
<223> OTHER INFORMATION: Albumin Binding Peptide

<400> SEQUENCE: 15

```
Gln Gly Leu Ile Gly Asp Ile Cys Leu Pro Arg Trp Gly Cys Leu Trp
1               5                   10                  15
Gly Arg Ser Val Lys
            20
```

<210> SEQ ID NO 16
<211> LENGTH: 15
<212> TYPE: PRT
<213> ORGANISM: Artificial Sequence
<220> FEATURE:
<223> OTHER INFORMATION: Albumin Binding Peptide

<400> SEQUENCE: 16

```
Glu Asp Ile Cys Leu Pro Arg Trp Gly Cys Leu Trp Glu Asp Asp
1               5                   10                  15
```

<210> SEQ ID NO 17
<211> LENGTH: 18
<212> TYPE: PRT
<213> ORGANISM: Artificial Seqeuence
<220> FEATURE:
<223> OTHER INFORMATION: Albumin Binding Peptide

<400> SEQUENCE: 17

```
Arg Leu Met Glu Asp Ile Cys Leu Pro Arg Trp Gly Cys Leu Trp Glu
1               5                   10                  15
Asp Asp
```

<210> SEQ ID NO 18
<211> LENGTH: 16
<212> TYPE: PRT
<213> ORGANISM: Artificial Sequence
<220> FEATURE:
<223> OTHER INFORMATION: Albumin Binding Peptide

<400> SEQUENCE: 18

```
Met Glu Asp Ile Cys Leu Pro Arg Trp Gly Cys Leu Trp Glu Asp Asp
1               5                   10                  15
```

```
<210> SEQ ID NO 19
<211> LENGTH: 15
<212> TYPE: PRT
<213> ORGANISM: Artificial Sequence
<220> FEATURE:
<223> OTHER INFORMATION: Albumin Binding Peptide

<400> SEQUENCE: 19

Met Glu Asp Ile Cys Leu Pro Arg Trp Gly Cys Leu Trp Glu Asp
1               5                   10                  15

<210> SEQ ID NO 20
<211> LENGTH: 18
<212> TYPE: PRT
<213> ORGANISM: Artificial Sequence
<220> FEATURE:
<223> OTHER INFORMATION: Albumin Binding Peptide

<400> SEQUENCE: 20

Arg Leu Met Glu Asp Ile Cys Leu Ala Arg Trp Gly Cys Leu Trp Glu
1               5                   10                  15

Asp Asp

<210> SEQ ID NO 21
<211> LENGTH: 20
<212> TYPE: PRT
<213> ORGANISM: Artificial Sequence
<220> FEATURE:
<223> OTHER INFORMATION: Albumin Binding Peptide

<400> SEQUENCE: 21

Glu Val Arg Ser Phe Cys Thr Arg Trp Pro Ala Glu Lys Ser Cys Lys
1               5                   10                  15

Pro Leu Arg Gly
            20

<210> SEQ ID NO 22
<211> LENGTH: 20
<212> TYPE: PRT
<213> ORGANISM: Artificial Sequence
<220> FEATURE:
<223> OTHER INFORMATION: Albumin Binding Peptide

<400> SEQUENCE: 22

Arg Ala Pro Glu Ser Phe Val Cys Tyr Trp Glu Thr Ile Cys Phe Glu
1               5                   10                  15

Arg Ser Glu Gln
            20

<210> SEQ ID NO 23
<211> LENGTH: 11
<212> TYPE: PRT
<213> ORGANISM: Artificial Sequence
<220> FEATURE:
<223> OTHER INFORMATION: Albumin Binding Peptide

<400> SEQUENCE: 23

Glu Met Cys Tyr Phe Pro Gly Ile Cys Trp Met
1               5                   10

<210> SEQ ID NO 24
<211> LENGTH: 235
<212> TYPE: PRT
<213> ORGANISM: Artificial Sequence
<220> FEATURE:
<223> OTHER INFORMATION: 497Fab-His Heavy Chain
```

<400> SEQUENCE: 24

```
Glu Val Gln Leu Val Glu Ser Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Gly Leu Glu Trp Val
        35                  40                  45

Gly Ser Ile Asn Phe Ala Gly Asp Ile Ser Tyr Tyr Arg Glu Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Asp Ala Asn Arg Gln Asn Tyr Asp Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His His His His His His His
225                 230                 235
```

<210> SEQ ID NO 25
<211> LENGTH: 218
<212> TYPE: PRT
<213> ORGANISM: Artificial Sequence
<220> FEATURE:
<223> OTHER INFORMATION: 497Fab-His Light Chain

<400> SEQUENCE: 25

```
Ala Ile Gln Leu Thr Gln Ser Pro Ser Ser Leu Ser Ala Ser Val Gly
1               5                   10                  15

Asp Arg Val Thr Ile Thr Cys Lys Ala Ser Glu Ser Val Ser Ser Ser
            20                  25                  30

Met Tyr Ser Tyr Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Trp
                85                  90                  95

Thr Ala Pro Arg Thr Phe Gly Gln Gly Thr Lys Val Glu Ile Lys Arg
            100                 105                 110
```

-continued

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 26
<211> LENGTH: 235
<212> TYPE: PRT
<213> ORGANISM: Artificial Sequence
<220> FEATURE:
<223> OTHER INFORMATION: 497dsFab-His Heavy Chain

<400> SEQUENCE: 26

Glu Val Gln Leu Val Glu Ser Gly Gly Gly Leu Val Lys Pro Gly Gly
1               5                   10                  15

Ser Leu Arg Leu Ser Cys Ala Ala Ser Gly Val Ile Phe Ser Asp Tyr
            20                  25                  30

Tyr Met Ala Trp Val Arg Gln Ala Pro Gly Lys Cys Leu Glu Trp Val
        35                  40                  45

Gly Ser Ile Asn Phe Ala Gly Asp Ile Ser Tyr Tyr Arg Glu Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Lys Thr Glu Asp Thr Ala Val Tyr Tyr Cys
                85                  90                  95

Thr Thr Asp Ala Asn Arg Gln Asn Tyr Asp Trp Phe Ala Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His His His His His His
225                 230                 235

<210> SEQ ID NO 27
<211> LENGTH: 218

```
<212> TYPE: PRT
<213> ORGANISM: Artificial Sequence
<220> FEATURE:
<223> OTHER INFORMATION: 497dsFab-His Light Chain

<400> SEQUENCE: 27

Ala Ile Gln Leu Thr Gln Ser Pro Ser Ser Leu Ser Ala Ser Val Gly
1               5                   10                  15

Asp Arg Val Thr Ile Thr Cys Lys Ala Ser Glu Ser Val Ser Ser Ser
            20                  25                  30

Met Tyr Ser Tyr Met His Trp Tyr Gln Gln Lys Pro Gly Lys Ala Pro
        35                  40                  45

Lys Leu Leu Ile Tyr Arg Ala Ser Asn Leu Glu Ser Gly Val Pro Ser
50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Trp
                85                  90                  95

Thr Ala Pro Arg Thr Phe Gly Cys Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215

<210> SEQ ID NO 28
<211> LENGTH: 234
<212> TYPE: PRT
<213> ORGANISM: Artificial Sequence
<220> FEATURE:
<223> OTHER INFORMATION: 652Fab-His Heavy Chain

<400> SEQUENCE: 28

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Tyr
            20                  25                  30

His Val Gln Trp Ile Arg Gln Pro Pro Gly Lys Ala Leu Glu Trp Leu
        35                  40                  45

Gly Val Met Trp Ser Asp Gly Asp Thr Ser Phe Asn Ser Val Leu Lys
50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Gly Thr Ile Ala Ala Met Asp Tyr Phe Asp Tyr Trp Gly Gln
            100                 105                 110
```

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His His His His His His His His
225                 230

<210> SEQ ID NO 29
<211> LENGTH: 214
<212> TYPE: PRT
<213> ORGANISM: Artificial Sequence
<220> FEATURE:
<223> OTHER INFORMATION: 652Fab-His Light Chain

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Ser Asn Tyr
            20                  25                  30

Leu Ala Trp Tyr Gln Gln Lys Pro Gly Lys Ala Pro Lys Leu Leu Ile
        35                  40                  45

Tyr His Thr Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Arg Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 30

<211> LENGTH: 234
<212> TYPE: PRT
<213> ORGANISM: Artificial Sequence
<220> FEATURE:
<223> OTHER INFORMATION: 652dsFab-His Heavy Chain

<400> SEQUENCE: 30

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Tyr
            20                  25                  30

His Val Gln Trp Ile Arg Gln Pro Pro Gly Lys Cys Leu Glu Trp Leu
        35                  40                  45

Gly Val Met Trp Ser Asp Gly Asp Thr Ser Phe Asn Ser Val Leu Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Gly Thr Ile Ala Ala Met Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His His His His His His His His
225                 230
```

<210> SEQ ID NO 31
<211> LENGTH: 214
<212> TYPE: PRT
<213> ORGANISM: Artificial Sequence
<220> FEATURE:
<223> OTHER INFORMATION: 652dsFab-His Light Chain

<400> SEQUENCE: 31

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Ser Asn Tyr
            20                  25                  30

Leu Ala Trp Tyr Gln Gln Lys Pro Gly Lys Ala Pro Lys Leu Leu Ile
        35                  40                  45

Tyr His Thr Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Arg Phe Pro Leu
```

-continued

```
                85                     90                      95
Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

DISULFIDE STABILIZED ANTIBODIES AND FRAGMENTS THEREOF

This application is a national phase entry of International Application No. PCT/GB2011/050608, filed Mar. 25, 2011, which claims the benefit of Great Britain Application No. 1005064.9, filed Mar. 25, 2010, the disclosures of which are incorporated by reference herein.

The present disclosure relates to antibodies and fragments thereof, wherein the variable regions therein are stabilised by an interchain disulfide bond there between, use of the same in therapy, in particular therapy by inhalation and pharmaceutical compositions comprising the same.

Fab and Fab' molecules are well known in the field of biotherapeutics and a number formats have been proposed to address various problems. In essence they are an "antibody" where the constant region —$CH_2CH_3$ in the heavy chain is absent. The "prime" element refers to the presence of a hinge portion. The present inventors believe that it has never been proposed to prepare a Fab or Fab' characterized in that a disulfide bridge is present between the variable regions of a heavy and light chain pairing therein.

The present inventors believe that a disulfide bond between the variable regions stabilizes the Fab/Fab' making the final entity more robust. The implications are wide ranging in that it may result in a longer shelf for the formulations comprising the modified Fab/Fab'. Additionally it allows new kinds of formulations of the Fab/Fab' to be prepared, for example formulations for topical delivery to the lungs, such as formulations for nebulization.

Topic delivery to the lungs is an important area of therapy because it allows rapid and direct delivery to the target organ, whilst simultaneously minimizing undesirable side effects. Some of the most useful and successful therapies are delivered topically to the lungs. In addition disease in the lungs and respiratory illness constitutes a significant burden to health authorities. In 2007 more than 160,390 people were expected to die from lung cancer in the US alone and in 2006 more than 39,000 cases of lung cancer were diagnosed in the UK. Similarly asthma is a significant problem with an estimated 100 million suffers worldwide. Other respiratory disease include COPD, emphysema, and chronic bronchitis. In 2000 the World Health organization estimated that 2.74 million people died of COPD worldwide.

Clearly effective treatment of these patients represents a significant challenge and anything that can be done to facilitate their treatment would be very useful. To date very few biotherapies have been available for respiratory treatment. Generally antibodies and antibody fragments are administered by infusion. The present invention aims to push the boundaries of respiratory medicine further by providing biological molecules which are suitable for use in respiratory therapy.

Thus the present inventors provide an antibody or antibody fragment comprising a Fab molecule having a light and a heavy chain, wherein the light chain variable region, $V_L$ and the heavy chain variable region, $V_H$, are linked by one or more disulfide bonds.

The disulfide bond between the $V_H$ and $V_L$ pair seems to aid general stability of the molecules, for example it aids the chemical and/or physical stability of the molecule. The presence of the disulfide bond(s) may result in a higher Tm, when the molecules are analysed by a suitable technique such as Thermofluor or Differential Scanning Calorimetry (DSC), than the Tm observed in corresponding molecules where the disulfide bond is absent. An increased chemical stability may also result in an increased thermal stability, for example the molecule with disulfide bonds presents may denature at a higher temperature than a molecule where the disulfide bonds are absent. The disulfide bond between $V_H$ and $V_L$ may also minimize inappropriate aggregation, for example when the molecule is formulated.

Antibody Fab fragments of the present invention may be any heavy chain and light chain pair having a variable ($V_H$/$V_L$) and constant region ($C_H$/$C_L$).

In one embodiment the format of the present invention consists of a Fab fragment.

In one embodiment the format of the present invention consists of a Fab' fragment.

In one embodiment the format of the present invention consists of a diFab fragment.

In one embodiment the heavy and light chain pair $V_H$/$C_{H1}$ and $V_L$/$C_L$ is covalently linked through interchain cysteines in the heavy and light chain constant regions.

The variable domains are provided in each chain such that they form pre-defined pairs with suitable/adequate binding to a target antigen.

In one embodiment, a Fab molecule according to the present invention has one, two or three, such as one disulfide bond between the $V_H$ and $V_L$ pair or each pair.

It will be appreciated that a Fab molecule as described herein may form part of another antibody molecule or antibody fragment. For example the heavy chain of the Fab fragment may be extended by one or more amino acids to create a Fab' fragment.

In one example, the present invention provides a Fab' fragment having a heavy and light chain pair, wherein the heavy and light chain variable regions of the heavy and light chain pair are linked by a disulphide bond.

In one example the present invention provides a complete antibody molecule comprising two Fab molecules wherein at least one of the Fab molecules is a Fab molecule according to the present invention. In one example the present invention provides a complete antibody molecule comprising two Fab molecules wherein both Fab molecules are Fab molecules according to the present invention. i.e. in one Example the present invention provides a complete antibody molecule having two heavy and light chain pairs wherein the heavy and light chain variable regions of each heavy and light chain pair are linked by a disulphide bond. In one example only one of the heavy and light chain variable region pairs are linked by a disulphide bond.

In one example the present invention provides a $F(ab)_2$ fragment comprising two Fab molecules wherein at least one of the Fab molecules is a Fab molecule according to the present invention. In one example the present invention provides a $F(ab)_2$ fragment comprising two Fab molecules wherein both of the Fab molecules are Fab molecules according to the present invention. i.e in one Example the present invention provides a $F(ab)_2$ having two heavy and light chain pairs wherein the heavy and light chain variable regions of each heavy and light chain pair are linked by a disulphide bond. In one example only one of the heavy and light chain variable region pairs are linked by a disulphide bond.

Suitable variable domains pairs may be identified by any means possible, for example including generation of antibodies in hosts and screening of B cells. Alternatively suitable pairs may be identified by phage display. In one embodiment the variable domain pair has affinity for a target antigen of 100 nM or less, such as 50 nM or less, in particular 1 nM or less.

The antibody molecules and variable domain pairs of use in the present invention can be from any species but are preferably derived from a monoclonal antibody, a human antibody, or are humanised fragments. An antibody fragment for use in the present invention can be derived from any class (e.g. IgG, IgE, IgM, IgD or IgA) or subclass of immunoglobulin molecule and may be obtained from any species including for example mouse, rat, shark, rabbit, pig, hamster, camel, llama, goat or human.

In one embodiment, the antibody or antibody fragment e.g. Fab or Fab' is a monoclonal, fully human, humanized or chimeric antibody fragment. In one embodiment the antibody or antibody fragment e.g. Fab or Fab' fragments are fully human or humanised.

Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO 92/02551, WO2004/051268 and WO2004/106377.

Humanized antibodies are antibody molecules from non-human species having one or more complementarity determining regions (CDRs) from the non-human species and a framework region from a human immunoglobulin molecule (see, for example, U.S. Pat. No. 5,585,089).

The antibodies for use in the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO 90/02809; WO 91/10737; WO 92/01047; WO 92/18619; WO 93/11236; WO 95/15982; and WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108. Also, transgenic mice, or other organisms, including other mammals, may be used to generate humanized antibodies.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced for example by the phage display methods described above and antibodies produced by mice in which the murine immunoglobulin variable and/or constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 B1 and EP0463151 B1.

The antibody Fab or Fab' fragment starting material for use in the present invention may be obtained from any whole antibody, especially a whole monoclonal antibody, using any suitable enzymatic cleavage and/or digestion techniques, for example by treatment with pepsin. Alternatively, or in addition the antibody starting material may be prepared by the use of recombinant DNA techniques involving the manipulation and re-expression of DNA encoding antibody variable and/or constant regions. Standard molecular biology techniques may be used to modify, add or delete amino acids or domains as desired. Any alterations to the variable or constant regions are still encompassed by the terms 'variable' and 'constant' regions as used herein.

The antibody fragment starting material may be obtained from any species including for example mouse, rat, rabbit, hamster, camel, llama, goat or human. Parts of the antibody fragment may be obtained from more than one species, for example the antibody fragments may be chimeric. In one example, the constant regions are from one species and the variable regions from another. The antibody fragment starting material may also be modified. In another example, the variable region of the antibody fragment has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibody fragments are well known in the art (see for example, Boss et al., U.S. Pat. No. 4,816,397; Cabilly et al., U.S. Pat. No. 6,331,415; Shrader et al., WO 92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment the variable domain pair forming a binding domain is a cognate pair. Cognate pair as employed herein is intended to refer to a natural pair of variable domains, that is to say isolated from a single antibody or antibody expressing cell.

In one example the cognate pair is a complementary $V_H/V_L$ pair which binds the antigen co-operatively i.e. they are a complementary $V_H/V_L$ pair.

Typically the cognate pair will be a $V_H/V_L$ pair derived from the same antibody. In one example the cognate pair are a pair of variable domains isolated as a pair from a 'library of pairs', such as a Fab phage display library.

In one example the $V_H/V_L$ pair are monospecific.

Variable domains may have been optimized and/or humanized.

Optimised/humanized variable domains derived from a cognate pair will still be considered a cognate pair after optimization/humanization.

Thus the invention extends to human, humanized or chimeric molecules.

In one embodiment a disulfide bond between a VH and VL pair may correspond to the pairs of positions between (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100b+V_L49$;

$V_H98+V_L46$ see for example Protein Science 6, 781-788 Zhu et al (1997);

$V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994); or $V_H106+V_L57$ see for example FEBS Letters 377 135-139 Young et al (1995).

The amino acid pairs listed above are in the positions conducive to replacement by cysteines such that a disulfide bond can be formed. Cysteines can be engineered into these desired positions by known techniques. In one embodiment therefore an engineered cysteine according to the present invention refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N.Y., 1989; Ausbel et al., Current Protocols in Molecular Biology, Greene Publishing & Wiley-Interscience, N.Y., 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

Accordingly in one embodiment a variable domain pair $(V_H/V_L)$ of the present invention may be linked by a disulfide bond between two cysteine residues, one in $V_H$ and one in $V_L$, wherein the position of the pair of cysteine residues is selected from the group consisting of $V_H37$ and $V_L95$, $V_H44$ and $V_L100$, $V_H44$ and $V_L105$, $V_H45$ and $V_L87$, $V_H100$ and $V_L50$, $V_H100b$ and $V_L49$, $V_H98$ and $V_L46$, $V_H101$ and $V_L46$, $V_H105$ and $V_L43$ and $V_H106$ and $V_L57$.

In one embodiment a variable domain pair $(V_H/V_L)$ of the present invention may be linked by a disulfide bond between two cysteine residues, one in $V_H$ and one in $V_L$, which are outside of the CDRs wherein the position of the pair of cysteine residues is selected from the group consisting of $V_H37$ and $V_L95$, $V_H44$ and $V_L100$, $V_H44$ and $V_L105$, $V_H45$ and $V_L87$, $V_H100$ and $V_L50$, $V_H98$ and $V_L46$, $V_H105$ and $V_L43$ and $V_H106$ and $V_L57$.

In one embodiment a variable domain pair $(V_H/V_L)$ of the present invention may be linked by a disulfide bond between two cysteine residues, one in $V_H$ and one in $V_L$, which are outside of the CDRs wherein the position of the pair of cysteine residues is selected from the group consisting of $V_H37$ and $V_L95$, $V_H44$ and $V_L105$, $V_H45$ and $V_L87$, $V_H100$ and $V_L50$, $V_H98$ and $V_L46$, $V_H105$ and $V_L43$ and $V_H106$ and $V_L57$.

In one embodiment a variable domain pair $(V_H/V_L)$ of the present invention may be linked by a disulfide bond between two cysteine residues wherein the cysteine residue of $V_H$ is at position 44 and the cysteine residue of $V_L$ is at position 100.

Typically the cysteine pairs are engineered into those positions in $V_H$ and $V_L$, accordingly in one embodiment a variable domain pair $(V_H/V_L)$ of the present invention may be linked by a disulfide bond between two engineered cysteine residues, one in $V_H$ and one in $V_L$, wherein the position of the pair of engineered cysteine residues is selected from the group consisting of $V_H37$ and $V_L95$, $V_H44$ and $V_L100$, $V_H44$ and $V_L105$, $V_H45$ and $V_L87$, $V_H100$ and $V_L50$, $V_H100b$ and $V_L49$, $V_H98$ and $V_L46$, $V_H101$ and $V_L46$, $V_H105$ and $V_L43$ and $V_H106$ and $V_L57$.

In one embodiment a variable domain pair $(V_H/V_L)$ of the present invention may be linked by a disulfide bond between two engineered cysteine residues, one in VH and one in VL, which are outside of the CDRs wherein the position of the pair of engineered cysteine residues is selected from the group consisting of $V_H37$ and $V_L95$, $V_H44$ and $V_L100$, $V_H44$ and $V_L105$, $V_H45$ and $V_L87$, $V_H100$ and $V_L50$, $V_H98$ and $V_L46$, $V_H105$ and $V_L43$ and $V_H106$ and $V_L57$.

In one embodiment the variable domain pair $(V_H/V_L)$ is linked by a disulfide bond between two engineered cysteine residues, one in $V_H$ and one in $V_L$, which are outside of the CDRs wherein the position of the pair of engineered cysteine residues is selected from the group consisting of $V_H37$ and $V_L95$, $V_H44$ and $V_L105$, $V_H45$ and $V_L87$, $V_H100$ and $V_L50$, $V_H98$ and $V_L46$, $V_H105$ and $V_L43$ and $V_H106$ and $V_L57$.

In one embodiment the variable domain pair $(V_H/V_L)$ is linked by a disulfide bond between two engineered cysteine residues wherein the engineered cysteine residue of $V_H$ is at position 44 and the engineered cysteine residue of $V_L$ is at position 100.

In one embodiment the molecule specifically binds a target antigen. Specifically binds as employed herein is intended to refer to molecules having high affinity for a target antigen (to which it is specific) and which binds antigens to which it is not specific with a low or much lower affinity (or not at all). Methods of measuring affinity are known to those skilled in the art and include such assays as BIAcore.

The antibody molecules of the present invention suitably have a high binding affinity, in particular, nanomolar or picomolar. Affinity may be measured using any suitable method known in the art, including BIAcore. In one embodiment the molecule of the present invention has a binding affinity of about 100 pM or better. In one embodiment the molecule of the present invention has a binding affinity of about 50 pM or better. In one embodiment the molecule of the present invention has a binding affinity of about 40 pM or better. In one embodiment the molecule of the present invention has a binding affinity of about 30 pM or better. In one embodiment the molecule of the present invention is fully human or humanised and has a binding affinity of about 100 pM or better.

In one embodiment there is provided a dimer of Fab' according to the present disclosure for example dimerisation may be through the hinge.

As is well known in the art, a typical Fab molecule comprises a heavy and a light chain pair in which the heavy chain comprises a variable region $V_H$ and a constant domain $CH_1$ and the light chain comprises a variable region $V_L$ and a constant domain CL.

In one embodiment the light chain(s) of the Fab comprises a single constant domain CL, for example a natural constant region derived from a light chain, e.g. kappa or lambda. In one embodiment the heavy chain of the Fab fragment comprises a single constant domain, for example a natural or modified $CH_1$ domain.

Constant domain as employed herein is intended to refer to CH$_1$, CH$_2$, CH$_3$ or a constant domain from a light chain. The molecules of the invention may include Fc regions i.e —CH$_2$CH$_3$ domains.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

In one embodiment a "natural" disulfide bond is present between the constant domain in the heavy and light chain, for example a disulfide bond, the interchain disulphide bond between CH$_1$ and CL is present. The CL domain is derived from either Kappa or Lambda. The natural position for a bond forming cysteine in the latter is 214 in human cKappa and cLambda (Kabat numbering 4$^{th}$ edition 1987). A disulfide bond or bond(s) in the constant region of the molecule is/are in addition to the at least one sulfide bond between a variable domain pair.

The exact location of the disulfide-bond-forming cysteine in the heavy chain constant domain such as CH$_1$ depends on the particular domain actually employed. Thus, for example in human gamma-1 the natural position of the disulfide bond is located position 233 (Kabat numbering 4$^{th}$ edition 1987). The position of the bond forming cysteine for other human isotypes such as gamma 2, 3, 4, IgM and IgD are know, for example 127.

In one embodiment the molecules according to the disclosure have a disulfide bond in a position equivalent or corresponding to that naturally occurring between the heavy chain constant region and the light chain constant region. Cysteines forming the bonds can be engineered into the domains as required.

In one embodiment a disulfide bond is present between the constant domain of the heavy and light chain in a non-naturally occurring position. This may be engineered into the molecule by introducing cysteine(s) into the amino acid chain at the positions required. This non-natural disulfide bond is in addition to or as an alternative to the natural disulfide bond present between the heavy and light chain constant domains.

In one embodiment no disulfide bond is present between the heavy and light chain constant domains, for example one or more of the cysteine residues may be replaced by another amino acid such as serine.

In one or more embodiments of Fab' molecules there are no interchain disulfide bonds in the hinge region.

Alternatively in one or more embodiments one or more (such as two) disulfide bonds are present in the hinge region, for example to allow formation of a F(ab')$_2$ or a complete antibody molecule.

In one embodiment a Fab' or F(ab')$_2$ molecule according to the present disclosure comprises a modified hinge.

A number of modified hinge regions have already been described for example, in U.S. Pat. No. 5,677,425, U.S. Pat. No. 6,642,356, WO9915549, WO2005003170, WO2005003169, WO2005003170, WO9825971 and WO2005003171 and these are incorporated herein by reference. The hinge will usually be located between the second variable domain in the heavy chain and the Fc region, where present. Particular examples of hinges include those shown in Table 1.

TABLE 1

Hinge sequences

| SEQ ID NO: | SEQUENCE |
|---|---|
| 1 | DKTHTCAA |
| 2 | DKTHTCPPCPA |
| 3 | DKTHTCPPCPATCPPCPA |
| 4 | DKTHTCPPCPATCPPCPATCPPCPA |
| 5 | DKTHTCPPCPAGKPTLYNSLVMSDTAGTCY |
| 6 | DKTHTCPPCPAGKPTHVNVSVVMAEVDGTCY |
| 7 | DKTHTCCVECPPCPA |
| 8 | DKTHTCPRCPEPKSCDTPPPCPRCPA |
| 9 | DKTHTCPSCPA |

The inventors believe that by providing variable domains as cognate pairs in the final construct optimizes and maintains the desirable antigen binding properties of the binding site formed by the relevant pair.

In one embodiment the antibody molecules of the present invention, in particular, Fab or Fab' molecules of the present invention comprise one or more albumin binding peptides. In vivo the peptide binds albumin, which increases the half-life of the molecule.

The albumin binding peptide may be appended from one or more variable regions, a hinge or C-terminal of the molecule or any location that does not interfere with the molecules antigen binding properties.

Examples of albumin binding peptides are provided in WO 2007/106120 and include:

TABLE 2

| SEQ ID NO: | SEQUENCE |
|---|---|
| 10 | DLCLRDWGCLW |
| 11 | DICLPRWGCLW |
| 12 | MEDICLPRWGCLWGD |
| 13 | QRLMEDICLPRWGCLWEDDE |
| 14 | QGLIGDICLPRWGCLWGRSV |
| 15 | QGLIGDICLPRWGCLWGRSVK |
| 16 | EDICLPRWGCLWEDD |
| 17 | RLMEDICLPRWGCLWEDD |
| 18 | MEDICLPRWGCLWEDD |
| 19 | MEDICLPRWGCLWED |
| 20 | RLMEDICLARWGCLWEDD |
| 21 | EVRSFCTRWPAEKSCKPLRG |
| 22 | RAPESFVCYWETICFERSEQ |
| 23 | EMCYFPGICWM |

It will be appreciated that one or more amino acid substitutions, additions and/or deletions may be made to the variable domains, provided by the present invention, without significantly altering the ability of the antibody molecule, in particular a Fab or Fab' to bind to target antigen and to neutralise activity thereof. The effect of any amino acid substitutions, additions and/or deletions can be readily tested by one skilled in the art, for example by using the in vitro assays, for example a BIAcore assay.

The constant region domains, in particular in the Fc domain, where present, employed in the present invention, may be selected having regard to the proposed function of the molecule, in particular the effector functions which may be required, and for example, may be human IgA, IgD, IgE, IgG or IgM domains. In particular, domains from human IgG may be used, especially of the IgG1 and IgG3 isotypes when the Fab or Fab' is intended for therapeutic uses and antibody effector functions are required. Alternatively, domains from IgG2 and IgG4 isotypes may be used when the Fab or Fab' is intended for therapeutic purposes and antibody effector functions are not required. It will be appreciated that sequence variants of these constant region domains may also be used. For example domains from IgG4 molecules in which the serine at position 241 has been changed to proline as described in Angal et al., Molecular Immunology, 1993, 30 (1), 105-108 may be used. It will also be understood by one skilled in the art that Fab or Fab' may undergo a variety of posttranslational modifications. The type and extent of these modifications often depends on the host cell line used to express the molecule as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995).

If desired a molecule for use in the present invention may be conjugated to one or more effector molecule(s). It will be appreciated that the effector molecule may comprise a single effector molecule or two or more such molecules so linked as to form a single moiety that can be attached to the antibody molecule in particular, Fab or Fab' of the present invention. Where it is desired to obtain a fragment according to the invention linked to an effector molecule, this may be prepared by standard chemical or recombinant DNA procedures in which the fragment is linked either directly or via a coupling agent to the effector molecule. Techniques for conjugating such effector molecules to Fab/Fab' are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the Fab/Fab' in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment of the disclosure and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example a Fab/Fab' for use in the present invention are attached to poly(ethyleneglycol) (PEG) moieties. In one particular example the Fab/Fab' is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO 98/25971). In one example the molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

The present invention also provides isolated DNA encoding an antibody molecule described herein or a fragment thereof, e.g. Fab or Fab'.

In a further aspect there is provided a vector comprising said DNA.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Molecule or fragment according to the present invention, are used interchangeably herein.

In a further aspect there is provided a host cell comprising said vector and/or DNA.

Any suitable host cell/vector system may be used for expression of the DNA sequences encoding the molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule as described herein comprising culturing a host cell containing a vector (and/or DNA) of the present invention under conditions suitable for leading to expression of protein from DNA encoding an antibody molecule of the present invention, and isolating an antibody molecule such as a Fab or Fab'.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibody molecules according to the present disclosure are expressed at suitable levels from host cells making them conducive to commercial processing.

The antibody molecules of the present invention are useful in the treatment and/or prophylaxis of a pathological condition.

Thus there is provided an antibody or antibody fragment comprising a Fab molecule according to the present invention for use in treatment, by administering a therapeutically effective amount thereof, for example in a pharmaceutical formulation. In one embodiment the antibody or antibody fragment according to the invention is administered topically to the lungs, for example by inhalation.

The present invention also provides a pharmaceutical or diagnostic composition comprising a molecule of the present invention in combination with one or more of a pharmaceutically acceptable excipient, diluent or carrier. Accordingly, provided is the use of a molecule of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the molecule of the present invention together with one or more of a pharmaceutically acceptable excipient, diluent or carrier.

The molecule of the disclosure may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the molecule or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhitor is a small molecule. In another embodiment the inhibitor is an antibody specific to the target.

The pharmaceutical compositions suitably comprise a therapeutically effective amount of the molecule of the invention. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which a molecule of the present invention is administered depends on the nature of the condition to be treated, for example the extent of the disease/inflammation present and on whether the molecule is being used prophylactically or to treat an existing condition.

The frequency of dose will depend on the half-life of the molecule and the duration of its effect. If the molecule has a short half-life (e.g. 2 to 10 hours) it may be necessary to give one or more doses per day. Alternatively, if the molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the molecule or fragment, for example if the pH of the formulation is 7 then a pI of from 8-9 or above may be appropriate. Whilst not wishing to be bound by theory it is thought that this may ultimately provide a final formulation with improved stability, for example the binding protein or fragment thereof remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms (for example lyophilised forms) suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be a molecule. As such, it will be susceptible to degradation in the gastrointestinal tract. Thus, if the composition is to be administered by a route using the gastrointestinal tract, the composition will need to contain agents which protect the binding protein from degradation but which release the molecule once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the binding protein or fragment) is of primary importance.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The molecule of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 mL of water so as to achieve a pH of about 4.0 to 5.0. A suspension or solution can be reconstituted, for example, lyophilised molecules.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the molecule in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) for example packed in foil envelopes. Each vial contains a unit dose in a volume, e.g., 2 mL, of solvent/solution buffer.

The molecules of the present disclosure are thought to be particularly suitable for delivery via nebulisation.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

BRIEF DESCRIPTION OF THE DRAWINGS

The following detailed description of the embodiments of the present invention can be best understood when read in conjunction with the following drawings, where like structure is indicated with like reference numerals and in which:

FIG. 1 shows the sequences for 497Fab-His (heavy chain—SEQ ID NO:24; light chain—SEQ ID NO:25); 497dsFab-His (heavy chain—SEQ ID NO:26; light chain—SEQ ID NO:27); 652Fab-His (heavy chain—SEQ ID NO:28;

light chain—SEQ ID NO:29); and 652dsFab-His (heavy chain—SEQ ID NO:30; light chain—SEQ ID NO:31).

EXAMPLE 1

Generation and Analysis of Disulphide Stabilized Fab-His

Construction of 652Fab-His, 652dsFab-His, 497Fab-His and 497dsFab-His plasmids

The light chain variable regions of 652 and 497 antibodies were cloned as HindIII/BsiW1 fragment into UCB's proprietary mammalian expression CKappa vector. The heavy chain variable regions of 652 and 497 antibodies were cloned as HindIII-Xho1 fragment into $CH_1$-His vector.

Disulphide stabilization by mutation to cysteine at position 44 of the heavy chain and 100 of the light chain were done using the QuikChange Lightening Site directed mutagenesis kit from Agilent Technologies, using the manufacturer's protocol. Two 30 base pair oligos were designed for introducing the cysteine mutation at the heavy 44 and light 100 amino acid positions. The disulphide stabilized constructs were verified by sequencing. The sequences for the antibody are shown in FIG. 1.

Mammalian Expression of 652Fab-His, 652dsFab-His, 497Fab-His and 497dsFab-His

HEK293 cells were transfected with the heavy and light chain plasmids using Invitrogen's 293fectin transfection reagent according to the manufacturer's instructions. Briefly, 5 µg heavy chain plasmid and 5 µg light chain plasmid were incubated with 10 µl 293fectin and 340 µl Optimem media for 20 mins at RT. The mixture was then added to $5 \times 10^6$ HEK293 cells in suspension and incubated for 4 days with shaking at 37° C. After 4 days the supernatant was collected by centrifugation at 1500×g to remove the cells and then 0.22 µm sterile filtered.

652Fab-His, 652dsFab-His, 497Fab-His and 497dsFab-His Quantification

The concentration of Fab or dsFab in the mammalian supernatants may be measured using a sandwich ELISA. The Fab or dsFab in the sample is captured with an anti-$CH_1$ antibody and detected with an anti-kappa-HRP conjugate. The detection antibody is then developed with TMB and the concentration of the unknown samples calculated from a standard curve.

652Fab-His, 652dsFab-His, 497Fab-His and 497dsFab-His Purification

The 652Fab-His, 652dsFab-His, 497Fab-His and 497dsFab-His in the supernatants were purified by Ni affinity chromatography. To the appropriate number of wells of a Qiagen 96 well filter plate was added 150 µl of a 50% slurry of NiNTI superflow and the unused wells were covered with a plate seal. −0.5 Bar vacuum was applied using a Millipore vacuum manifold. To each well was added 800 µl of 50 mM sodium phosphate, 300 mM sodium chloride, pH 8 buffer and a −0.5 Bar vacuum was applied. To each well was added 800 µl of 250 mM imidazole, 50 mM sodium phosphate, 300 mM sodium chloride, pH 8 buffer and a −0.5 Bar vacuum was applied. To each well was added 800 µl of 50 mM sodium phosphate, 300 mM sodium chloride, pH 8 buffer and a −0.5 Bar vacuum was applied. To each well was added 800 µl of 50 mM sodium phosphate, 300 mM sodium chloride, pH 8 buffer and a −0.5 Bar vacuum was applied. To each sterile filtered supernatant was added a $10^{th}$ volume of 100 mM imidazole, 0.5M sodium phosphate, 1.5M sodium chloride, pH 8 buffer. 800 µl of the conditioned supernatants were applied to the wells, left for 5 minutes and then a −0.5 Bar vacuum was applied. This was repeated until all the condition supernatant had been applied. The wells were washed by the addition of 800 µl of 20 mM imidazole, 50 mM sodium phosphate, 300 mM sodium chloride, pH 8 buffer and a −0.5 Bar vacuum was applied. The wash step was repeated 3 times. A clean 96 deep well plate was placed under the filter plate and the Fab-His was eluted into this plate by the addition of 100 µl of 250 mM imidazole, 50 mM sodium phosphate, 300 mM sodium chloride, pH 8 buffer to the filter plate wells followed by application of a −0.5 Bar vacuum.

Thermofluor Thermal Stability Assay

Samples (1 µl of sample at ~1 mg/ml, 8 µl of PBS and 1 µl of 30× stock of Sypro orange fluorescent dye) may be run in quadruplicate in 384 well plates. The plate is heated from 20-99° C. using a 7900HT fast real-time PCR system and the fluorescence (excitation at 490 nm, emission at 530 nm) measured. The data is processed and the inflection point for unfolding calculated.

The invention claimed is:

1. An antibody or antibody fragment comprising at least one Fab molecule, wherein said fab molecule comprises one or more disulfide bonds present between variable domains of heavy and light chain pairing therein and wherein no disulfide bond is present between heavy and light chain constant domains of said Fab molecule.

2. The antibody or antibody fragment according to claim 1, wherein the antibody or antibody fragment is selected from the group consisting of a Fab, a Fab', a F(ab)$_2$ and a complete antibody molecule.

3. The antibody or antibody fragment according to claim 1, wherein the antibody or antibody fragment comprises two Fab molecules, wherein in each Fab molecule, one or more disulfide bonds are present between a light chain variable region, $V_L$ and a heavy chain variable region, $V_H$.

4. The antibody or antibody fragment according to claim 3, wherein the antibody or antibody fragment is the complete antibody molecule or a F(ab)$_2$.

5. The antibody or antibody fragment according to claim 1 wherein, the molecule further comprises an albumin binding peptide.

6. The antibody or antibody fragment according to claim 1, wherein one disulfide bond is present between the light chain variable region, $V_L$ and the heavy chain variable region, $V_H$ of the Fab molecule.

7. The antibody or antibody fragment according to claim 1, wherein one disulfide bond is present between each light chain variable region, $V_L$ and the heavy chain variable region, $V_H$ pairing of the antibody or fragment.

8. A composition comprising the antibody or antibody fragment according to claim 1, and a pharmaceutically acceptable excipient.

9. The antibody or antibody fragment according to claim 1 or a composition comprising an antibody or antibody fragment according to claim 1, and a pharmaceutically acceptable excipient for use in treatment or prophylaxis.

10. A method of treatment comprising administering a therapeutically effective amount of an antibody or fragment as defined in claim 1 or a composition comprising an antibody or fragment according to claim 1, and a pharmaceutically acceptable excipient.

11. The antibody or antibody fragment according to claim 1 or a composition comprising an antibody or antibody fragment according to claim 1 for the manufacture of a medicament.

12. The antibody or antibody fragment according to claim 1, wherein the disulfide bond is between two cysteine residues, one in the $V_L$ and one in the $V_H$, wherein the cysteine in the $V_L$ is at position 100 and the cysteine in the $V_H$ is at position 44.

13. An antibody or antibody fragment comprising at least one Fab molecule, wherein said fab molecule comprises one or more disulfide bonds present between variable domains of heavy and light chain pairing therein, wherein no disulfide bond is present between heavy and light chain constant domains of said Fab molecule and wherein the molecule further comprises an albumin binding peptide.

* * * * *